United States Patent [19]

Mertens et al.

[11] Patent Number: 5,185,579
[45] Date of Patent: Feb. 9, 1993

[54] DETECTION AND RANGING OF MATERIAL FLAWS USING MICROWAVE TRANSMISSION LINE REFLECTOMETRY

[75] Inventors: Donald B. Mertens, Thousand Oaks; Louis E. Gates, Jr., Westlake Village; Ronald I. Wolfson, Los Angeles; William W. Milroy, Playa del Rey; Joseph P. Smalanskas, Westchester, all of Calif.

[73] Assignee: Hughes Aircraft Company, Los Angeles, Calif.

[21] Appl. No.: 738,388

[22] Filed: Jul. 31, 1991

[51] Int. Cl.$^5$ .......................................... G01R 31/11
[52] U.S. Cl. ................................. 324/527; 324/533; 324/637; 333/238
[58] Field of Search ............... 324/527, 533, 534, 637, 324/642; 333/1, 238

[56] References Cited

U.S. PATENT DOCUMENTS

| | | | |
|---|---|---|---|
| 3,753,086 | 8/1973 | Shoemaker, Jr. | 324/533 |
| 4,123,703 | 10/1978 | Robinson | 324/632 |
| 4,739,276 | 4/1988 | Graube | 324/642 X |
| 4,743,887 | 5/1988 | Pothier | 324/642 X |
| 4,949,076 | 8/1990 | Wann | 324/533 X |
| 5,034,708 | 7/1991 | Adamian et al. | 324/637 X |

Primary Examiner—Jack B. Harvey
Assistant Examiner—Glenn W. Brown
Attorney, Agent, or Firm—L. A. Alkov; W. K. Denson-Low

[57] ABSTRACT

A structure integrity monitoring apparatus and method for use with certain structures such as air-frame structures. A meandering transmission line (22) or serpentine coaxial cable is adhered to a dielectric substrate (20). The dielectric substrate may be a composite panel of the air-frame structure. A microwave signal is introduced at one end of the transmission line (22) or coaxial cable and absorbed at the other end by an appropriate signal absorbing device. For use of the meandering transmission line (22), generally two conductors (22, 24) are affixed on opposite sides of the dielectric substrate (20). In this manner, an electric field created by the two conductors (22, 24) by the microwave signals propagating through them is confined within the dielectric substrate (20). As the signals travel down the transmission conductors (22, 24), they will be reflected at crossover points along the way creating a signature reflection wave. If the dielectric substrate is flawed, a perturbation in the electric field caused by the flaw will create a reflection of the microwave signal at the flaw area. When this reflection signal is compared with the signature signal, it can be determined where and if a flaw is present.

32 Claims, 3 Drawing Sheets

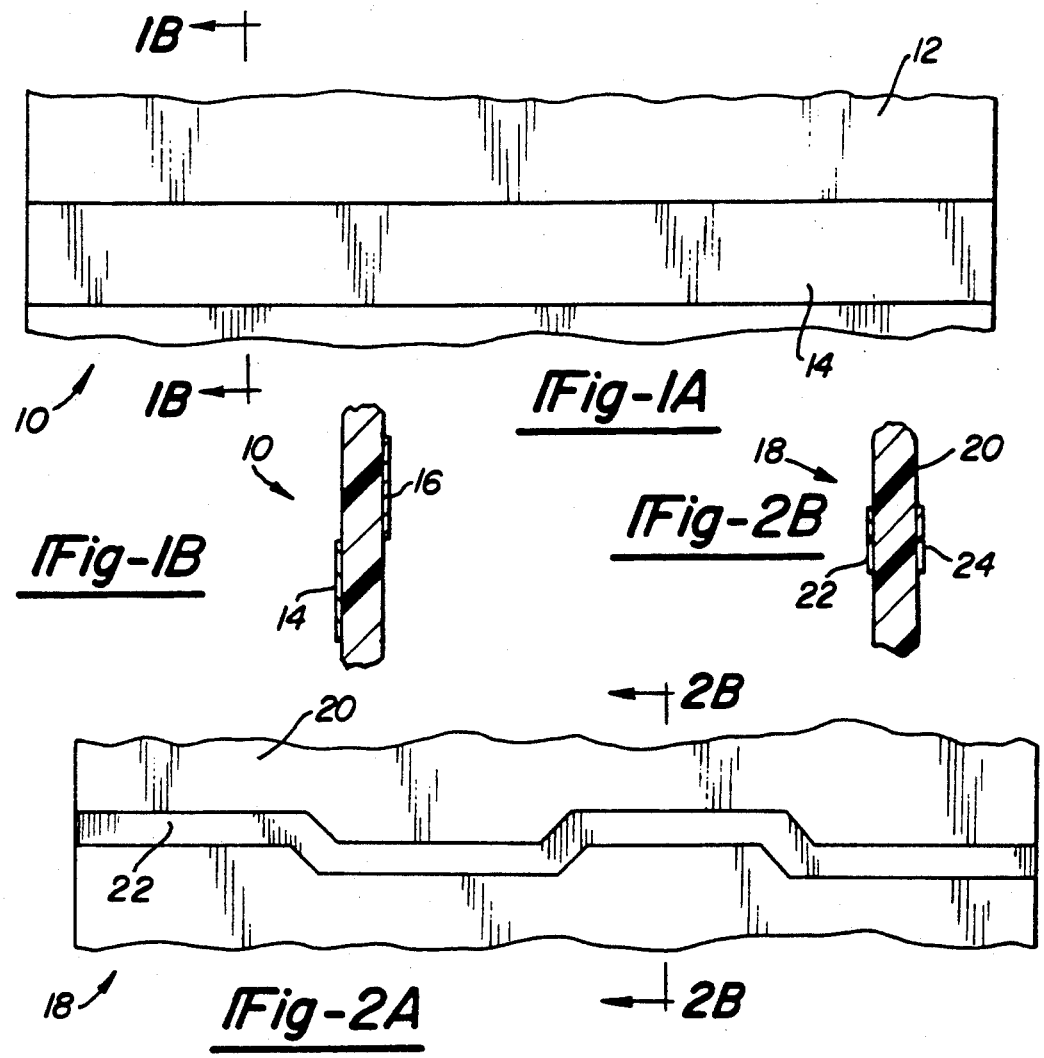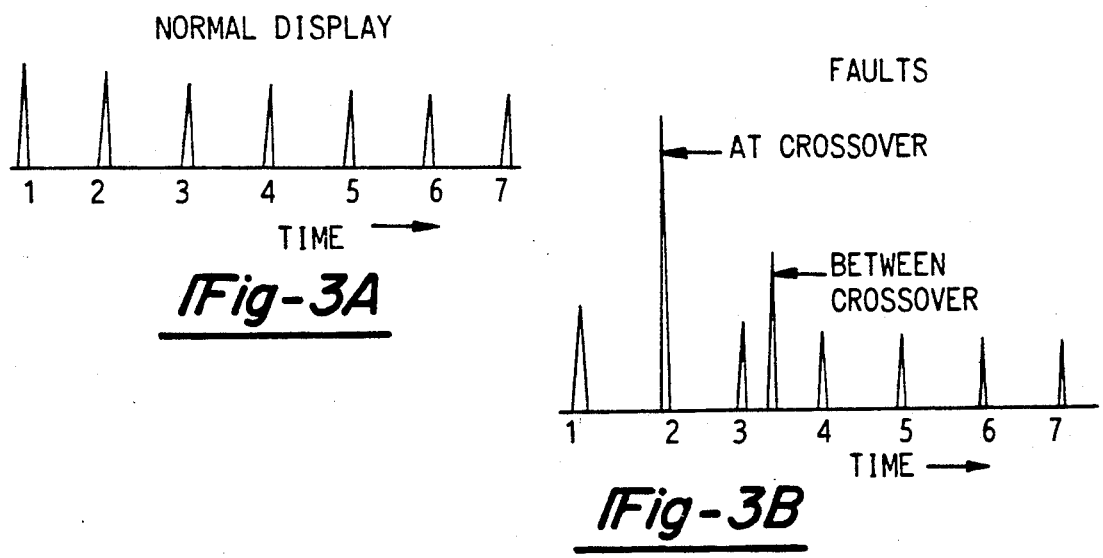

DETECTION AND RANGING OF MATERIAL FLAWS USING MICROWAVE TRANSMISSION LINE REFLECTOMETRY

BACKGROUND OF THE INVENTION

1. Field of the Invention

This invention relates generally to a sensor for detecting the presence of defects, and more specifically, to a sensor for detecting defects in an air-frame structure by means of meandering transmission lines.

2. Discussion

It is well known that air travel puts a large amount of structural stress on air-frame structures. Since the air-frame structure is repeatedly administered to these stresses it eventually becomes very susceptible to certain defects or flaws such as material fatigue, loosened connections, delaminations, etc., thus affecting the integrity of the aircraft. In addition, flaws from in-flight incidents, such as impacts with foreign objects and battle damage, could also provide problems in maintaining the aircraft in a safe condition. If these defects go unchecked or undetected, the eventual outcome could be catastrophic. It therefore becomes crucial to at least periodically check for defects within the air-frame structure, especially at high stress or flight critical locations.

Different methods are known in the art to detect the presence of flaws in an air-frame structure. These methods have included visual inspection for observing such things as loose rivets, buckled material and dents; strain gages for detecting the presence of certain distortions in structural members; and the use of ultrasonics and acoustics for administering sound waves to detect flaws by means of determining sound transmission quality. Generally, these procedures have not met with adequate success. For instance, visual inspection is limited by human skill and other obvious physical limitations, strain gages are not practical to position throughout all panel structures of an aircraft, and ultrasonics and acoustics are difficult to instrument in certain structures. In addition, many of these prior art methods require a certain amount of expertise and technical skill to adequately implement. Further problems arise in that many of these prior art methods do not provide the capability for both the continuous or the selective, such as in-flight, detection of flaws.

What is needed then is a sensor to detect structural flaws within an air-frame structure without the need to perform a technically intricate procedure, and further, to perform the detection continuously or at a desirable time. It is therefore an object of the present invention to provide such a sensor.

SUMMARY OF THE INVENTION

Disclosed is a sensor for detecting structural flaws in a variety of different types and shapes of structures. It is noted that the description herein will generally be described with reference to air-frame structures; however, the invention disclosed has universal application in many other structures such as in ships, railroad cars, trucks, automobiles, race cars, tank cars, space satellites, space vehicles, as well as in all types of industrial structures such as toxic waste and fuel tanks and bins for many types of processing equipment. In other words, the invention has application wherever structural integrity must be periodically or continuously assessed.

The invention includes at least one transmission line, such as a microstrip, slotline, coplanar waveguide, dielectric image guide or a coaxial cable, for guiding a propagating signal. Generally the transmission line is mounted to a substrate by appropriate means. The signal is introduced at one end of the transmission line and is absorbed at an opposite end. As the signal propagates, it creates an electric field in the dielectric. If while traveling along the transmission line the signal encounters a region in or near the dielectric with a dent, delamination or other such flaw that will cause a perturbation in the electric field around the transmission line, a discontinuity in the signal transmission will occur in the form of a reflection back to the transmitter from which the signal originated. By observing a reflected wave characteristic, the flaw can be detected and isolated.

In a first embodiment, electromechanical transmission lines are mounted on opposite sides of a dielectric substrate to form an unbalanced slotline configuration. The substrate is generally a section of the structure to be monitored. The transmission lines can be positioned in a meandering configuration or can be straight strip conductors. Generally, a microwave signal is introduced at one end of the transmission lines. At an opposite end of the transmission lines an absorption resistor is positioned to absorb the microwave signal. The propagation of the signals through the transmission lines creates an electric field which is confined within and extends completely through the dielectric substrate. For an unflawed substrate, the signal will be reflected at certain points, such as crossover points of the transmission lines, along the substrate to form a signal reflection signature. If a defect is present in the substrate, the electric field will be distorted and the reflection signal will be altered. By analyzing the reflection signal and comparing it to the reflection signature, it is possible to isolate an area on the structure which has been flawed.

Another embodiment includes use of a single microstrip transmission line mounted on a dielectric substrate. The substrate is either a section of the structure to be monitored or is a separate panel mounted by appropriate means to a structure to be monitored. By this, the microstrip can be appended to an already existing structure such as an air-frame panel. The principle of detecting flaws with the microstrip is the same as with the unbalanced slotline configuration above. A signal is sent down the microstrip which creates an electric field in the dielectric substrate. If a defect is present in either the surrounding dielectric or metallic surface of the structure, a reflection will be sent back through the microstrip, thus representing detection of a flaw.

Additional objects, advantages, and features of the present invention will become apparent from the following description and appended claims, taken in conjunction with the accompanying drawings.

BRIEF DESCRIPTION OF THE DRAWINGS

FIGS. 1(a)–(b) show an unbalanced slotline detector incorporating strip conductors;

FIGS. 2(a)–(b) show an unbalanced slotline detector incorporating meandering conductors;

FIGS. 3(a)–(b) show graphs of the reflection signal in an unflawed and a flawed state.

DETAILED DESCRIPTION OF THE PREFERRED EMBODIMENT

The following description of the preferred embodiments is merely exemplary in nature and is in no way intended to limit the invention or its application or uses.

Disclosed is an apparatus and method for detecting flaws in a certain structure, generally an air-frame structure. The apparatus incorporates transmission lines adhered to a dielectric substrate. A microwave signal is sent along the transmission lines at one end and is absorbed by an impedance matched absorption device at an opposite end. The propagation of the signal creates an electric field in the substrate. As the signal propagates through the transmission line it will travel substantially unimpeded if the transmission lines and the substrate are straight. If the transmission lines are altered or deformed in any manner, a wave will be reflected from the deformity and propagate through the transmission line opposite to the signal direction. The reflected wave can then be detected. Therefore, if a defect, such as a dent, is present in the substrate, the electric field will become distorted, and thus a reflection will occur in the signal path.

If the transmission lines are configured in a serpentine or meandering configuration, a reflection will occur each time the transmission line is turned. Consequently, a serpentine or meandering transmission line will create a signature pattern representative of the path of the transmission line as a result of the reflections. In a meandering configuration the transmission line can cover a wider or more traverse section of the substrate. In addition, the signature reflection wave developed by the meandering transmission lines creates a signal which includes an array of reflections depicting specific locations on the substrate. Therefore, a defect can be isolated by specific reflection locations in the reflected signal wave when compared with the signature pattern.

Figure 12:
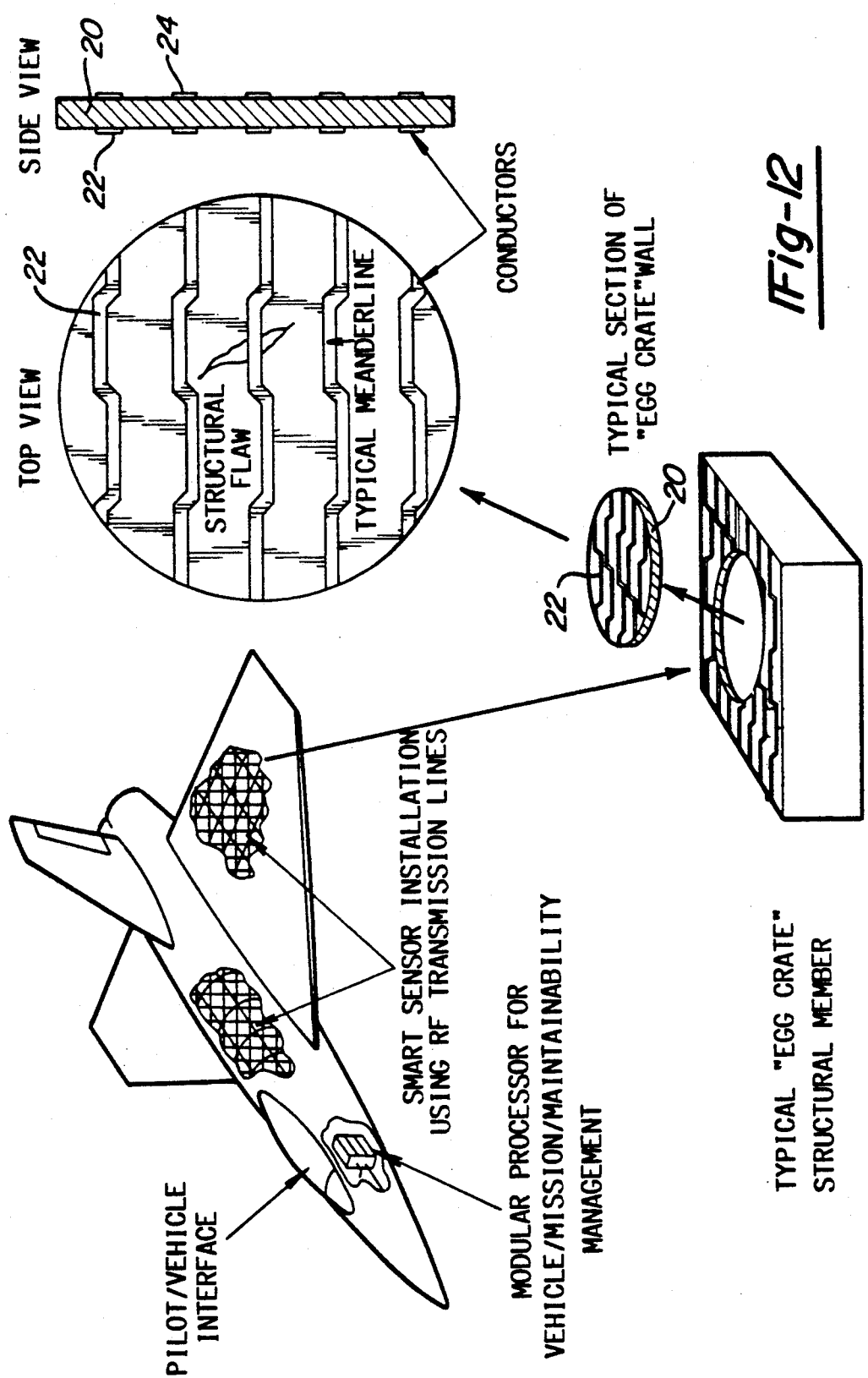
FIG. 12 illustrates an example of an installation of the detector of one embodiment of the detector of the present invention.

For example, FIG. 12 shows a typical "smart sensor" installation using RF transmission lines. The structural member shown in the detail employs an "egg crate" construction for simplicity, strength and lightweight. Meandering transmission lines 22 and 24 are depicted mounted on opposite sides of dielectric substrate 20 to form an unbalanced slotline configuration. A structural flaw in the substrate 20 will produce a distortion in the electric field of a microwave signal that propagates through transmission lines 22 and 24. The size and location of the defect can be assessed by comparing the reflection signature of the test signal to a reference signature stored for the undamaged structure.

Now turning to FIGS. 1(a)–(b) an unbalanced slotline detector 10 is shown in a side view in FIG. 1(a) and in cross section in FIG. 1(b). Unbalanced slotline detector 10 includes a substrate 12 comprised of a dielectric material. Generally, dielectric substrate 12 is a composite material which may be the structure which is desired to be observed for defects, such as a panel of a composite aircraft wing. Alternatively, substrate 12 may be a separate panel which is appropriately connected to the structure to be observed. Adhered to opposite sides of dielectric substrate 12 is a first transmission line 14 and a second transmission line 16. Transmission lines 14 and 16 are generally a strip of conductive material which may be applied to substrate 12 by spraying, adhered to substrate 12 by means of a dielectric adhesive, or applied by any other appropriate method. As is apparent from FIG. 1(b), transmission lines 14 and 16 are arranged in a parallel, unbalanced configuration on opposite sides of substrate 12. In this example, transmission line 14 and transmission line 16 are arranged such that they are not directly opposite each other on opposite sides of substrate 12.

In operation, an electromagnetic transmission signal is generally applied by means (not shown) well known to those skilled in the art to both transmission lines 14 and 16 at one end. Generally, the transmission signal is at a microwave frequency and can either be a broadband wave or a narrow frequency band. By limiting the frequency to a narrow range of wavelengths, intrusion of the sensor will be limited to a small range of the frequency spectrum. At an opposite end of transmission lines 14 and 16 is a signal absorber (not shown) such as an impedance matched absorption resistor. As the electromagnetic signal propagates along transmission lines 14 and 16, an electric field is created within and extended through dielectric substrate 12 between transmission lines 14 and 16. It is noted that it is possible to create an electric field within dielectric substrate 12 by only producing a signal on one of the transmission lines 14 or 16. In that configuration, the other transmission line will act as a ground conductor to form the electric field within the substrate. If the microwave signal is only applied to one of the transmission lines, a current will be induced in the other transmission line. The currents in each of the transmission lines will be traveling in opposite directions. The use of an unbalanced configuration enables the electric field to be confined within substrate 12. A balanced configuration, i.e., positioning the transmission lines on the same side of the substrate, creates electric field fringing outside of the dielectric substrate and beyond the gap region between the transmission lines, and is therefore limited in its application.

If substrate 12 and transmission lines 14 and 16 are reasonably smooth, the signal will travel along substantially unimpeded. In the event that dielectric substrate 12 is bent or dented or the like, the electric field across dielectric substrate 12 will be distorted. The distortion will cause a reflected wave traveling opposite to the signal path. By incorporating the necessary devices to detect the reflected wave, it is therefore possible to detect for substantially any defect which distorts the electric field.

FIGS. 2(a)–2(b) show a second unbalanced slotline detector 18 incorporating a dielectric substrate 20 and dual meandering transmission lines 22 and 24. Meandering transmission lines 22 and 24 are positioned on opposite sides of dielectric substrate 20 as shown in FIG. 2(b). In distinction from FIG. above, transmission lines 22 and 24 are centered on opposite sides of substrate 20 and are positioned in a meandering configuration, i.e., they are arranged in a back and forth path. It is noted that transmission lines 14 and 16 can be meandering lines and transmission lines 22 and 24 can be straight conductors or either can be other types of mix and matched transmission lines if desirable.

In operation of the meandering unbalanced slotline detector 18, a microwave signal is sent along both meandering transmission lines 22 and 24 as with transmission lines 14 and 16 above. This signal is also absorbed by an absorption resistor at an opposite end. Since the transmission lines 22 and 24 are in a meandering configuration, each ti⁻ e the signal hits a crossover point in the transmission line it sends back a reflection signal towards the signal generator. The reflected signal creates a signature pattern of the meandering path of the transmission line. Once again, a defect in the dielectric substrate 20 will create a perturbation in the electric field created by the two transmission lines 22 and 24, and thus will also create a separate reflection signal other than those of the natural propagation of the meandering transmission lines 22 and 24.

By positioning transmission lines 22 and 24 on opposite sides of substrate 20 or transmission lines 14 and 16 on opposite sides of substrate 12, the desirabilities of having an unbalanced slotline sensor are realized. The desirable key features of the unbalanced slotline detector are that the electric field is essentially confined within the dielectric substrate, the electric field extends through the substrate from one transmission line to the other, and the transmission lines are external to the dielectric substrate; thus, they do not interfere with the substrate and are easily accessible for repair.

In FIGS. 3(a)-3(b), a graph of the reflection wave is shown for a meandering transmission line configuration, such as transmission lines 22 and 24. In FIG. 3(a), the horizontal axis represents a time relationship for a device detecting reflections from one of either transmission lines 22 or 24. A separate graph could be calculated from the reflections along the other transmission line. The detection device is generally a time domain reflectometer (TDR). As is apparent, each spike at a designated reference location represents a reflection at a crossover point or turn of the transmission line. If the crossover points of the meandering transmission line is at regular intervals, the reflection spikes will also occur at regular intervals. However, it is not critical that the meandering lines have crossovers at regular intervals, and in some design it may be desirable to have irregular crossover intervals. As is also apparent, as time increases, the reflection spikes will occur from crossover points farther down the transmission lines, and thus will be reduced in amplitude due to line losses. FIG. 3(a) is thus a signature reflection wave representation.

FIG. 3(b) shows defect reflection spikes along with the normal signature spikes of the reflection wave of FIG. 3(a). As is apparent, the reflection spike at crossover point 2 in FIG. 3(b) is of greater amplitude than the reflection spike at crossover point 2 in FIG. 3(a), and therefore represents a defect at this crossover point. In addition, a defect is shown between crossover points 3 and 4 on the same graph. This represents a defect at a location between crossover points 3 and 4 represented by the third and fourth crossover points of the meandering transmission line. By this it is clear that a defect location can be isolated by determining at what points on the graph the reflections occur.

Figure 4:
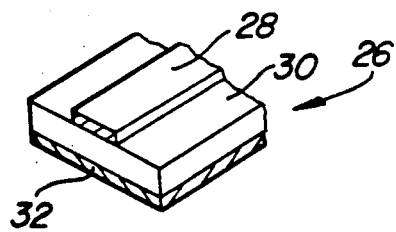
FIGS. 4–11 show different embodiments of certain microstrip detector configurations.

FIGS. 4-11 represent other embodiments of the invention incorporating alternate configured transmission lines for different type designs. The principles of each embodiment are substantially the same. In FIG. 4, a microstrip sensor 26 is shown including a ground plate 32 having a dielectric composite panel 30 adhered to one side of it, and a transmission strip 28 adhered to a side of dielectric panel 30 opposite ground plate 32. Generally, in this embodiment, the dielectric composite panel 30 would be a segment of the structure which was desired to be assessed for defects. Here, since the ground plane is a conductor, the electric field created by a signal propagating through transmission line 28 would be essentially confined within the dielectric panel 30 representing the composite structure of the apparatus, such as an aircraft. As above, a deformity in panel 30 would provide a perturbation in the electric field, which would create a reflection in the transmission signal.

The sensor of FIG. 4 is also applicable if used without the ground plate 32. If ground plate 32 were removed, the signal traveling through transmission strip 28 would provide fringing fields within the panel 30, which could provide perturbations in the field if the panel 30 was damaged. In addition, a second composite panel could be placed over transmission strip 28 and adhered to panel 30. In this configuration, a series of conductive strips or filaments could be positioned within a panel to monitor for defects.

Figure 5:
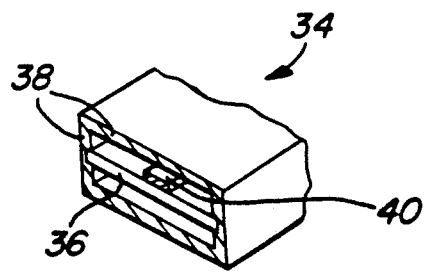

FIG. 5 shows a suspended stripline sensor 34. Stripline sensor 34 includes a substrate 36 surrounded by a conductive waveguide structure 38 such that airgaps are formed between substrate 36 and conductive waveguide structure 38 on both sides of substrate 36 substantially as shown. Substrate 36 is attached to conductive waveguide structure 38 at opposite edges. Adhered to one side of substrate 36 is a transmission strip 40. An appropriate signal propagating through transmission strip 40 will create an electric field within the airgaps created by conductive waveguide structure 38 around substrate 36. Waveguide structure 38 helps shape a desirable field around transmission strip 40. Consequently, any perturbation in the electric field will register as a reflected wave through transmission strip 40.

Figure 6:
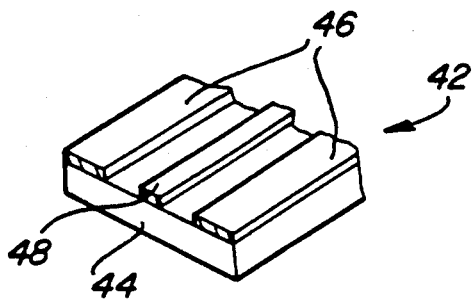

Now turning to FIG. 6, a coplanar waveguide sensor 42 is shown. Waveguide sensor 42 includes a substrate 44 on which are positioned a series of transmission strips. Two transmission strips 46 are arranged on opposite edges of a top surface of substrate 44. A third transmission strip 48 is aligned between transmission strips 46 such that airgaps are created between each of the transmission strips. Therefore, if an appropriate signal is sent along transmission strip 48, an electric field will be created between strip 48 and the other two strips 46 within the airgaps. Fringing fields will also be formed within substrate 44. It is noted that transmission strips 46 need to be properly grounded in order to induce the current within them to develop the electric field. Accordingly, any perturbation in the electric field will be registered as a reflected signal along transmission strip 44.

Figure 7:
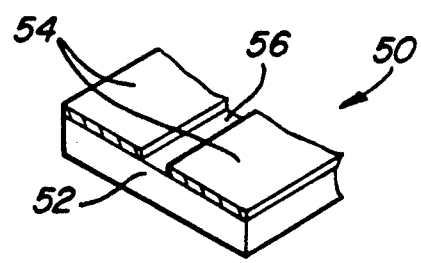

Now turning to FIG. 7, a balanced slotline sensor 50 is shown which is similar to the coplanar waveguide sensor 42 of FIG. 6. Slotline sensor 50 incorporates a dielectric substrate 52 on which are positioned two conductive transmission strips 54 creating a slot 56 or airgap between them. A transmission signal sent along either one of transmission strips 54 will create an electric field within slot 56 as with sensor 42. As above, certain defects can be detected which create perturbations in the electric field.

Figure 8:
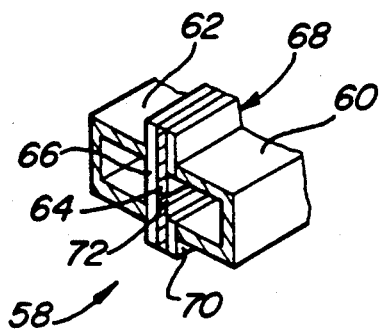

Now turning to FIG. 8, a finline sensor 58 is shown. Finline sensor 58 includes two U-shaped metal portions 60 and 62 forming a waveguide structure. The portions 60 and 62 are separated by a sandwiched structure 68 as shown. The sandwiched structure 68 includes conductive fins 64 between a dielectric substrate 66 on one side and a dielectric substrate 70 on the opposite side. Dielectric substrate 70 is shown cutaway to expose a slot 72 between conductive fins 64. Conductive fins 64 act as the transmission line for accepting the signal. The electric field is cre ted within slot 72 and shaped by the U-shaped metal portions 60 and 62.

Figure 9:
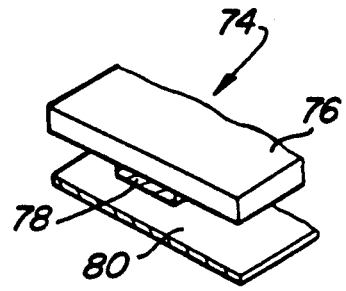
Figure 10:
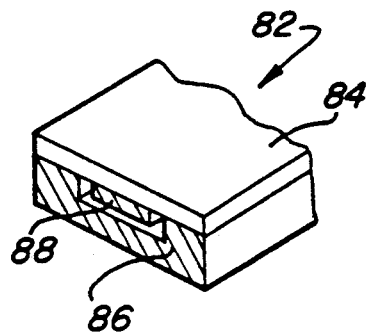

FIGS. 9 and 10 disclose two inverted microstripline sensors. Specifically, FIG. 9 shows an inverted microstripline sensor 74 comprised of a substrate 76 having a microstrip transmission line 78 on one side. Adjacent transmission line 78 and opposite to substrate 76 is a planar conductive portion 80. An airgap is created between transmission line 78 and planar portion 80. If an appropriate signal is introduced along transmission line 78 an electric field will be created in this airgap.

FIG. 10 is a trapped inverted microstripline sensor 82 incorporating a substrate 84 similar to substrate 76 and a microstrip transmission line 88 similar to transmission line 78. In this embodiment, however, the conductive portion is a U-shaped section whose legs connect to substrate 84, and which surround transmission line 88 substantially as shown. An airgap is still created on three sides of transmission line 88.

Figure 11:
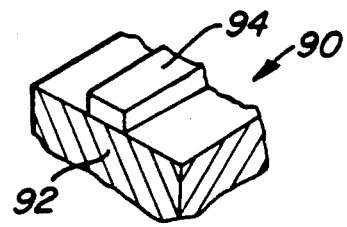

FIG. 11 is a dielectric image guide 90 which includes a conductive substrate 92 having a dielectric strip 94 adhered to one side of it. The microwave signal is introduced into dielectric strip 94. Conductive substrate 92 prevents strip 94 from being lossy.

An additional configuration to that of structure 26 would be to replace transmission line 28 with a coaxial cable (not shown) or an array of coaxial cables. Further, the coaxial cable network can be configured into a serpentine array to achieve the desirabilities of the meandering transmission lines as discussed above. In this embodiment, it would not be necessary to include a ground plane. A coaxial cable has the benefit that it can create its own electric field within the dielectric medium. However, certain drawbacks exist with the coaxial cable configuration. Specifically, the electromagnetic field created by the coaxial cable is confined entirely within the outer conducting shielding of the coaxial cable unless it is breached or improperly grounded. This drawback can be alleviated by grounding the center conductor and carrying the signal on the outer conductor of the coaxial cable. A second approach would be to make a "leaky" coaxial cable. This is accomplished in a variety of different ways, such as with an outer conductor of a loose braid or closely wound helix. Alternatively, the outer conductor can be made thin compared to the "skin depth" at the operating frequency of the signal. The amount of electric field leaking through a shield of given thickness could then be adjusted by tweaking the operating frequency. Impinging signals at much lower frequencies would not propagate within the coaxial cable as a required field cannot be supported by the electrically thin field. Signals at much higher frequencies could not penetrate a shield that appears to be "many skin depths" thick. However, a drawback of the "leaky" coaxial cable sensor is that it does not combine the electric field within the composite panel.

Microwave frequencies generally offer the best frequency for assessing defects in a structure. As a rule of thumb, the nominal operating frequency should be chosen such that the dielectric substrate appears to be about ¼th wavelengths thick. Further, the above described sensor provides a certain amount of efficiency for detecting flaws in a structure in that the sampling rate can be at desirable periods of time. In other words, interrogation of the integrity of the structure can be performed at effective intervals, such as at the conclusion of a flight. In addition, such interrogations can be made at many specific sensor panels located on the aircraft, or at a central distribution point of fan-out to all the sensor panels mounted on the aircraft. If real time signal processing is available, continuous in-flight interrogation can be made so as to detect incurred flaws from vehicle maneuvering stresses, foreign object impact or battle damage.

The foregoing discussion discloses and describes merely exemplary embodiments of the present invention. One skilled in the art will readily recognize from such discretion, and from the accompanying drawings and claims, that various changes, modifications and variations can be made therein without departing from the spirit and scope of the invention as defined in the following claims.

What is claimed is:

1. A defect sensor comprising:
   a first dielectric substrate including a first side and a second side; and
   a first transmission line positioned on said first side of said dielectric substrate, said first transmission line positioned to accept a microwave signal at one end such that propagation of the microwave signal creates an electric field around the transmission line such that a perturbation in the electric field causes a reflection wave in the microwave signal, wherein the perturbation is representative of a defect; and
   a second transmission line positioned on said second side of said dieelectric substrate, said second transmission line also positioned to accept a microwave signal at one end, and wherein the combination of signals through the first and second transmission lines creates an electric field completely traversing and substantially confined within the substrate such that a defect in the substrate creates a perturbation in the electric field.

2. The sensor according to claim 1 wherein said first transmission line and said second transmission line are not positioned directly opposite to each other.

3. The sensor according to claim 1 wherein said first transmission line and said second transmission line are positioned substantially opposite to each other.

4. The sensor according to claim 1 wherein each of said first and second transmission lines are meandering transmission lines such that they create crossover points wherein each crossover point creates a reflected signal which produces a characteristic reflection wave.

5. The sensor according to claim 1 wherein each of said first and second transmission lines are conductive strips.

6. The sensor according to claim 1 further comprising a conductive ground plate, said ground plate positioned on said second side of said substrate opposite to said transmission line, wherein the combination of the ground plate and the signal propagating through the transmission line create an electric field completely through the substrate.

7. The sensor according to claim 1 wherein the transmission line is a microstrip.

8. The sensor according to claim 1 wherein an end of said transmission line opposite to the end which accepts the signal includes a signal absorption resistor for absorbing the microwave signal.

9. The sensor according to claim 1 wherein the first transmission line is a coaxial cable, said coaxial cable being a leaky coaxial cable such that an electric field is created in the dielectric substrate when the signal propagates through the coaxial cable.

10. The sensor according to claim 9 wherein the coaxial cable is an array of coaxial cables configured in a serpentine fashion on said substrate.

11. The sensor according to claim 1 wherein the dielectric substrate is a composite panel of an air-frame structure.

12. The sensor according to claim 1 further comprising a conductive waveguide, said conductive waveguide substantially encircling the substrate and connected to the substrate in at least one location, wherein the first transmission line is positioned within the waveguide such that there is no contact between the transmission line and the conductive waveguide.

13. The sensor according to claim 1 further comprising a second transmission line and a third transmission line, wherein said first, second and third transmission lines are microstrips, the second and third microstrip transmission lines positioned on opposite sides of the first microstrip transmission line on the first side of the dielectric substrate such that an airgap is created between the first transmission line and the second transmission line and the first transmission line and the third transmission line, said electric field being created within the airgaps when the signal propagates through the first transmission line.

14. The sensor according to claim 1 further comprising a second transmission line wherein said first and second transmission lines are microstrips, said first and second microstrip transmission lines positioned on first side of said substrate such that an airgap is created between them, said electric field being created within the airgap when the signal propagates through at least one of the transmission lines.

15. The sensor according to claim 1 further comprising a second dielectric substrate, a first conductive portion and a second conductive portion wherein said first and second conductive portions are configured in substantially U-shaped configurations such that the first U-shaped conductive portion is adhered to the second side of the first dielectric substrate and the second U-shaped conductive portion is adhered to the second substrate, said first transmission line including two fin transmission strips forming a slot, said fin transmission strips positioned between the first and second substrate, said electric field being created within the first and second conductive portions.

16. The sensor according to claim 1 further comprising a conductive layer, said conductive layer positioned adjacent the first transmission line substantially opposite the dielectric substrate such that an airgap is created between the first transmission line and the conductive layer, said electric field being created within the airgap.

17. The sensor according to claim 16 wherein the conductive layer is a U-shaped conductive portion such that the legs of the U-shaped conductive portion contacts the substrate on opposite sides of the first transmission line such that an airgap is created on each side of the first transmission line which does not contact the conductive portion, said electric field being created within the airgap.

18. The sensor according to claim 1 wherein the first dielectric substrate is a conductive substrate and the first transmission line is a dielectric transmission line.

19. A method of detecting flaws in a structure, said method comprising the steps of:
   positioning a first transmission line on a first side of a dielectric substrate;
   introducing a microwave signal into one end of said first transmission line to create an electric field;
   absorbing said microwave signal at an opposite end of said transmission line; and
   determining a reflection pattern of the microwave signal as it propagates through the transmission line, such that if a perturbation in the electric field occurs the microwave signal will be reflected; and
   positioning a second transmission line on a second side of said substrate and introducing a microwave signal into said second transmission line at one end and absorbing the microwave signal at an opposite end, such that the combination of the microwave signals through the first and second transmission lines creates an electric field entirely through the substantially confined within the substrate.

20. The method of claim 19 wherein the steps of positioning the first and second transmission lines on opposite sides of the substrate includes positioning the first transmission line and the second transmission line in a configuration such that they are not directly opposite to each other.

21. The method of claim 20 wherein the steps of positioning the first and second transmission lines includes positioning the first and second transmission lines substantially directly opposite from each other.

22. The method according to claim 19 wherein the step of positioning the first transmission line includes positioning the transmission line in a meandering fashion.

23. The method according to claim 19 wherein the step of positioning the first transmission line includes positioning at least one coaxial cable in a serpentine fashion.

24. The method according to claim 19 further comprising the steps of positioning a first U-shaped conductive portion such that the legs of the conductive portion contact a second side of the substrate and positioning a second U-shaped conductive portion adjacent the first transmission line such that an electric field is created within the first and second conductive portions.

25. The method according to claim 19 wherein the step of positioning the first transmission line includes positioning a microstrip transmission line.

26. The method according to claim 25 wherein the step of positioning a microstrip transmission line includes positioning three microstrip transmission lines on the first side of the dielectric substrate such that an airgap is created between each of the transmission lines.

27. The method according to claim 26 wherein the step of positioning the first transmission line includes positioning two microstrip transmission lines such that an airgap is created between the microstrip transmission lines.

28. The method according to claim 26 further comprising the step of positioning a conductive portion adjacent the first transmission line such that an airgap is created between the first transmission line and the conductive portion.

29. The method according to claim 28 wherein the conductive portion contacts the substrate on opposite sides of the first transmission line such that an airgap is created between the conductive portion and the transmission line on all sides of the transmission line which do not contact the conductive portion.

30. A defect sensor comprising:
   a dielectric substrate including a first side and a second side;
   a first transmission line positioned on said first side of said dielectric substrate, said transmission line positioned to accept a microwave signal at one end; and a second transmission line positioned on said second side of said dielectric substrate, said second transmission line also positioned to accept a microwave signal at one end;

wherein the propagation of the microwave signals through the first and second transmission lines creates an electric field completely through and substantially confined within the dielectric substrate and wherein a defect in the substrate creates a perturbation in the electric field which causes a reflection wave in each of the microwave signals.

31. The defect sensor according to claim 30 wherein each of the first and second transmission lines are meandering transmission lines.

32. The defect sensor according to claim 30 wherein each of the first and second transmission lines are microstrip.

* * * * *